United States Patent [19]

Liberts et al.

[11] Patent Number: 4,554,393

[45] Date of Patent: Nov. 19, 1985

[54] TWO-STAGE PROCESS FOR CONVERTING PROPANE TO AROMATICS

[75] Inventors: Sandra Liberts, Springvale South; Jack G. Creer, Upwey; Thomas Mole, Kew, all of Australia

[73] Assignees: The Broken Hill Proprietary Company Limited, Melbourne; Commonwealth Scientific and Industrial Research Organisation, Campbell, both of Australia

[21] Appl. No.: 485,379

[22] Filed: Apr. 18, 1983

Related U.S. Application Data

[63] Continuation of Ser. No. 330,659, Dec. 14, 1981, abandoned.

[30] Foreign Application Priority Data

Dec. 19, 1980 [AU] Australia .............................. PE7041

[51] Int. Cl.$^4$ .......................... C07C 2/08; C07C 5/32
[52] U.S. Cl. .................................... 585/322; 585/315; 585/407; 585/415; 585/418; 585/424; 585/662
[58] Field of Search .............. 585/319, 322, 407, 415, 585/660, 662, 412, 418, 424, 315

[56] References Cited

U.S. PATENT DOCUMENTS

| | | | |
|---|---|---|---|
| 3,665,049 | 5/1972 | Cornelius et al. | 585/662 |
| 3,760,024 | 9/1973 | Cattanach | 585/415 |
| 4,032,589 | 6/1977 | Wall | 585/660 |
| 4,120,910 | 10/1978 | Chu | 585/417 |
| 4,191,637 | 3/1980 | Light et al. | 585/407 |
| 4,216,346 | 8/1980 | Antos | 585/660 |
| 4,288,645 | 9/1981 | Wagstaff | 585/415 |
| 4,291,182 | 9/1981 | Dautzenberg et al. | 585/415 |
| 4,293,722 | 10/1981 | Ward et al. | 585/315 |
| 4,304,948 | 12/1981 | Vora et al. | 585/315 |
| 4,417,083 | 11/1983 | Bernard et al. | 585/415 |

FOREIGN PATENT DOCUMENTS 0455920 4/1949 Canada .............................. 585/662

*Primary Examiner*—D. E. Gantz
*Assistant Examiner*—Anthony McFarlane
*Attorney, Agent, or Firm*—Murray, Whisenhunt and Ferguson

[57] ABSTRACT

A process for the production of aromatic compounds from low-molecular weight predominantly paraffinic feedstock which comprises contacting the feedstock in a first reactor with a dehydrogenation catalyst to produce a first reaction product containing alkenes; contacting said first reaction product in a second reactor with a crystalline aluminosilicate catalyst to produce a second reaction product containing aromatics; and separating an aromatic-rich fraction therefrom. In a preferred embodiment the feedstock consists essentially of propane and/or butane.

16 Claims, 1 Drawing Figure

TWO-STAGE PROCESS FOR CONVERTING PROPANE TO AROMATICS

This application is a continuation of U.S. application having Ser. No. 330,659, filed Dec. 14, 1981 now abandoned.

This invention relates to the production of aromatic compounds from low molecular-weight paraffins.

In this age of increased population, pollution and consumption of irreplaceable natural resources, it is important, if not mandatory, that processes for the production of aromatic compounds be energy efficient, in order to reduce the consumption of natural resources, yet at the same time produce a greater yield and less by-products, in order to meet the demands of a growing, fuel-consuming population and to reduce ever-increasing pollution problems.

The production of aromatic compounds from low molecular-weight paraffins is well known. However, such processes are not energy efficient and by no means produce what may be considered as high yields.

U.S. Pat. No. 3,374,281 describes a method of producing alkylated benzene compounds from $C_4$–$C_5$ paraffins and hydrogen, wherein said paraffins are alkylated within a temperature range of 426.7° C. to 648.9° C. and a pressure range of 0.014 to 3.45 MPa. However, this U.S. Patent does not teach conversion of propane.

Australian Pat. No. 484,974 discloses a process for the preparation of aromatic compounds from $C_2$–$C_4$ paraffins and/or olefins wherein the paraffins and/or olefins are brought into contact with a crystalline aluminosilicate of the ZSM-5 type.

Example 5 of Australian Pat. No. 484,974 illustrates the conversion of propane to a liquid aromatic product at a yield of 10 weight % wherein the reaction takes place at a temperature of 500° C., in the absence of added hydrogen, and at a pressure of 0.10 MPa (1 atm).

In addition, it may be experimentally shown that the conditions stated above in Australian Pat. No. 484,974 produce a significant proportion, approximately 10% of byproduct, namely $C_1$–$C_2$ alkanes.

Obviously, Australian Pat. No. 484,974 experiences serious limitations wherein a high temperature, yet lower than the temperature used in U.S. Pat. No. 3,374,281, produces a low yield and a significant proportion of feed material converted to $C_1$–$C_2$ alkanes, comparatively low-value hydrocarbons.

It is evident therefore, that although the production of aromatic compounds from low molecular-weight paraffins via various methods is well known in the art, none of the prior processes teach the production of aromatic compounds from low molecular-weight paraffins wherein a relatively low temperature is needed, thereby conserving energy, a high yield is obtained, thereby increasing the efficiency of production; the amount of relatively low-value by-product, $C_1$–$C_2$ alkanes, is minimized, thereby increasing production efficiency; and a major by-product is relatively high-value hydrogen, thereby providing an additional economic advantage.

It is an object of the present invention to provide a novel process for the production of aromatic compounds from low molecular-weight paraffins.

In a general aspect, the invention provides a process for the production of aromatic compounds from low molecular-weight paraffins including propane and butane.

In accordance with the invention, we provide a novel process for the production of aromatic compounds from low molecular-weight paraffins, which process comprises a two-stage reaction system to which an additional step of recycling may be added.

An embodiment of the invention comprises contacting, in a first reactor, low molecular-weight paraffin(s) with a dehydrogenation catalyst to produce alkene(s). The reaction product is passed into a second reactor, which reactor is charged with a crystalline aluminosilicate catalyst to produce aromatics. The reaction product of the second reactor is passed to a product separator wherein the predominently aromatic hydrocarbon liquid product of the second reactor is removed any any unconverted alkene and unreacted alkane are separated. After separation of hydrogen and $C_1$–$C_2$ hydrocarbons, $C_{3+}$ hydrocarbons are preferably recycled to the first reactor.

DESCRIPTION OF THE DRAWING

In FIG. 1, the feedstock (1) is introduced into the first reactor (2) wherein a dehydrogenation catalyst is utilized to convert the feed alkane(s) to corresponding alkene(s), to produce a product (3). Product (3) is passed to the second reactor (4), wherein a crystalline aluminosilicate catalyst is utilized to convert the alkene(s) to a product (5) containing aromatic compounds. Product (5) from the second reactor (4) is then passed to a product separator (6) in which the predominantly aromatic liquid hydrocarbon product is removed (7). Any hydrogen and $C_1$–$C_2$ hydrocarbons are extracted as product stream (8). Any unconverted alkene together with unreacted alkane is recycled back (9) to the first reactor (2).

Figure 1:
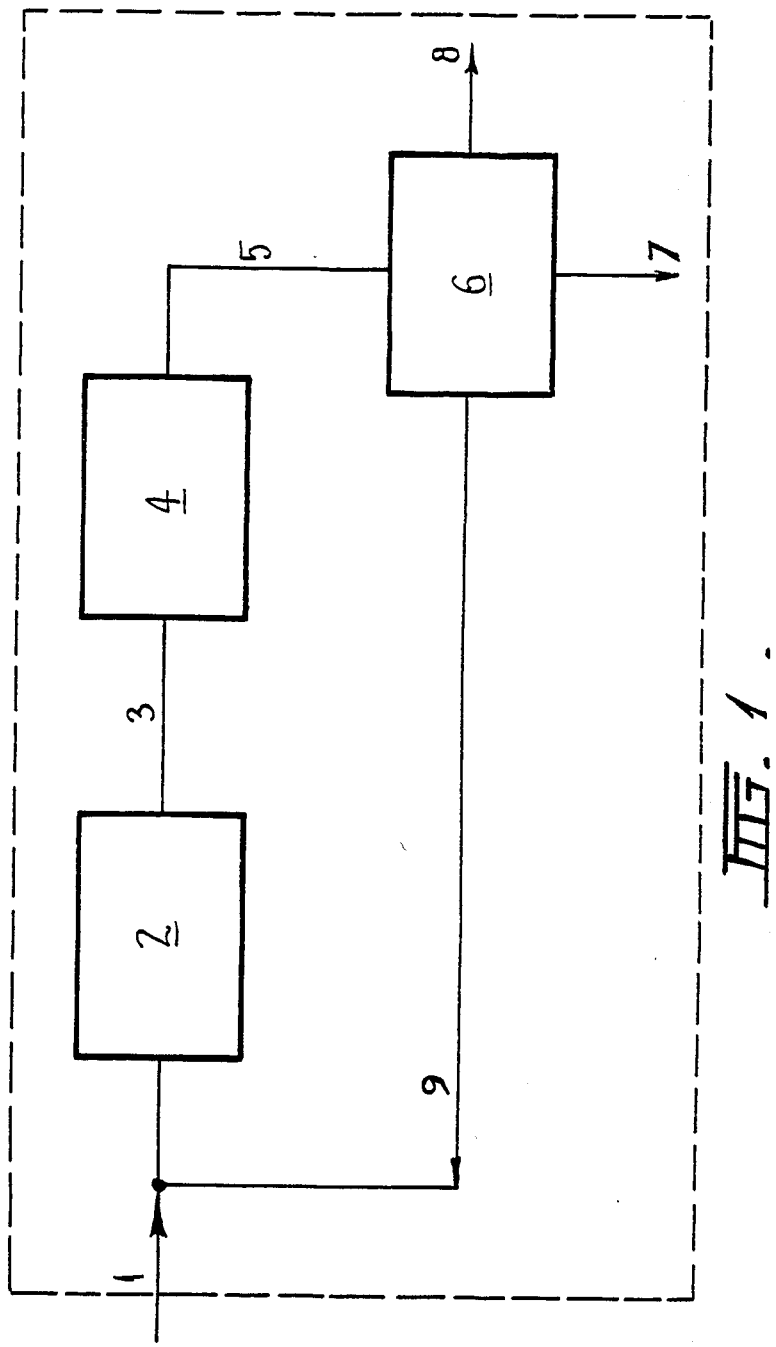
FIG. 1 is a flow sheet of the process and illustrates one example of the process according to the invention.

A preferred embodiment of the invention comprises contacting low molecular-weight paraffin(s) with a dehydrogenation catalyst, in a first reactor at a temperature of between 380° and 600° C., preferably between 450° and 550° C., a pressure of between 0.01 and 0.50 MPa and a mass space velocity of between 0.1 and 10 $hr^{-1}$. The following Table 1 illustrates the conditions and yields for the first reactor.

TABLE 1

| CONDITIONS AND YIELDS FOR REACTOR 1 | | | | | | |
|---|---|---|---|---|---|---|
| | Example | | | | | |
| | 1 | 2 | 3 | 4 | 5 | 6 |
| Feed | Propane | Propane | Propane | Propane | Propane | Propane |
| Catalyst (Chromia/Alumina) | Unpromoted | Potassium promoted | Cerium promoted | Potassium & cerium promoted | Potassium & cerium promoted | Potassium & cerium promoted |
| *Temperature °C. | 540/490 | 540/492 | 540/490 | 540/492 | 540/492 | 562/517 |
| MHSV ($hr^{-1}$) | 2.0 | 2.0 | 2.0 | 1.0 | 2.0 | 1.0 |
| Pressure MPa | 0.1 | 0.1 | 0.1 | 0.1 | 0.1 | 0.1 |
| Conversion (wt %) | 19.9 | 23.4 | 17.9 | 21.8 | 19.7 | 28.6 |

TABLE 1-continued

| | CONDITIONS AND YIELDS FOR REACTOR 1 | | | | | |
|---|---|---|---|---|---|---|
| | Example | | | | | |
| | 1 | 2 | 3 | 4 | 5 | 6 |
| **Selectivity to propane | .92 | .94 | .93 | .95 | .93 | .90 |

*Number to left of / denotes temperature outside reactor
Number to right of / denotes temperature inside reactor adjacent to catalyst bed.
**Selectivity defined as $\frac{\text{weight of propene produced}}{\text{total weight of hydrocarbons produced}}$ Preferably, the dehydrogenation catalyst is promoted chromia alumina.

More preferably, the dehydrogenation catalyst is a potassium and/or cerium promoted catalyst.

The reaction product of the first reactor is then passed into a second reactor which is charged with a crystalline aluminosilicate catalyst. In the second reactor the reaction takes place at a temperature between 220° and 550° C., preferably 300° to 460° C., a pressure of between 0.01 to 0.50 MPa and a mass space velocity of between 0.1 to 10 hr$^{-1}$.

Preferably, the crystalline aluminosilicate catalyst is of the ZSM-5 type. The catalyst may be modified by hydrogen, zinc or other metals or mixtures thereof.

The following Table 2 illustrates the conditions and yields for the second reactor.

matic selectivity was recorded with the propene/propane feed.

Example 7 of Table 2 used, in the second reactor, another sample of HZSM-5, prepared as described below, using a different seed from that used in the preparation of the catalyst of examples 1, 2 or 3. The results of the experiment show minimal propane conversion and almost complete propene conversion, with very low methane, ethane and ethylene selectivity, whilst maintaining good aromatic selectivity.

In the first, reactor, the operating conditions of the process are adjusted for maximum selectivity of alkene production rather than for maximum conversion of alkane(s).

In the second reactor, the operating conditions are set and maintained to provide high alkene conversion. Because of catalyst properties, high aromatic compound selectivity is achieved with especially good production of aromatic gasoline. We have established that the conditions of reaction can be chosen so that the conversion of the alkane(s) is kept low. Consequently, there is no significant production of the low value $C_1$-$C_2$ alkanes, from the original feed stock.

TABLE 2

| | CONDITIONS AND YIELDS FOR REACTOR 2 | | | | | | |
|---|---|---|---|---|---|---|---|
| | Example | | | | | | |
| | 1 | 2 | 3 | 4 | 5 | 6 | 7 |
| Feed | 20 wt % $C_3H_6$/ 80 wt % $C_3H_8$ | 20 wt % $C_3H_6$/ 80 wt % $C_3H_6$ | 20 wt % $C_3H_6$/ 80 wt % $C_3H_8$ | $C_3H_8$ | 20 wt % $C_3H_6$/ 80 wt % $C_3H_8$ | $C_3H_8$ | 20 wt % $C_3H_6$/ 80 wt % $C_3H_8$ |
| Catalyst | H—ZSM5 | H—ZSM5 | Zn—ZSM5 | Zn—ZSM5 | H—ZSM5 | H—ZSM5 | H—ZSM5 |
| *Temperature (°C.) | 550/500 | 405/371 | 445/401 | 445/401 | 500/473 | 500/493 | 353/310 |
| MHSV (Hr$^{-1}$) | 4 | 4 | 4 | 3 | 2.7 | 2.2 | 4 |
| Pressure (MPa) | 0.1 | 0.1 | 0.1 | 0.1 | 0.1 | 0.1 | 0.1 |
| Propane Conversion (%) | 12 | <1 | 8 | 13 | 10 | 19 | <1 |
| Propene Conversion (%) | 74 | 88 | 98 | N.A. | >98 | N.A. | >98 |
| **Selectivity to | | | | | | | |
| methane | 0.11 | <0.01 | 0.04 | 0.07 | 0.12 | 0.21 | 0.001 |
| ethylene | 0.21 | 0.08 | 0.02 | 0.03 | 0.07 | 0.10 | 0.009 |
| ethane | 0.08 | <0.01 | 0.07 | 0.16 | 0.18 | 0.24 | 0.005 |
| Aromatics | 0.36 | 0.31 | 0.63 | 0.54 | 0.32 | 0.11 | 0.35 |

*Number to left of / denotes temperature outside reactor
Number to right of / denotes temperature inside reactor adjacent to catalyst bed.
**Selectivity defined as $\frac{\text{weight of specified hydrocarbon produced}}{\text{total weight of hydrocarbons produced}}$ The first two examples given in Table 2 demonstrate the marked reduction in light hydrocarbon (methane, ethylene and ethane) selectivity when the second reactor temperature is set at the conditions as detailed in the description of the invention. They also show that the selectivity to aromatics is not significantly reduced.

Examples 3 and 4 of Table 2 used a zinc-exchanged catalyst, in the second reactor prepared as described hereunder, to show the improvement of the invention. With propene added to a feed gas of propane the selectivities toward the low value hydrocarbons especially methane and ethane are reduced by some 50%, even though the space velocity was increased and at the temperature used, some propane conversion was evident. Also the selectivity to aromatics is increased with the propene/propane feed, over that observed with a propane feed. Similarly examples 5 and 6 show improvements in the selectivities of the products of reaction when an acid-washed ZSM-5 catalyst was used in the second reactor. In this case a large increase in aro- We have shown that under recycle conditions, using propane feed and with the liquid product separator operating in such a manner that the aromatic products, together with other $C_5$ and $C_6$ hydrocarbons are removed, the product selectivities are methane: 0.05
ethylene: 0.02
ethane: 0.05
liquid: 0.76

The weight percentage of aromatic hydrocarbons in the liquid product was determined to be 62%. The experimental conditions used to derive these results were:

FIRST REACTOR catalyst: potassium and cerium chromia alumina
temperature: 540°/490° C.
pressure: 0.1 MPa

SECOND REACTOR catalyst: HZSM-5
temperature: 350°/310° C.
pressure: 0.1 MPa

The results given above highlight the invention showing the high selectivity towards aromatic rich liquid products and the low selectivity for the lower value low molecular weight hydrocarbons.

The catalysts employed in the first stage of this invention are well known and commercially available. For example promoted chromia alumina, referred to above, is described in an article by A. V. Grosse and V. N. Ipatieff, published in Industrial and Engineering Chemistry (February, 1940, pages 268 to 272). Crystalline aluminosilicate catalysts suitable for use in the second stage are described for example in Australian Application No. 35237/78 and Australian Pat. No. 487,817.

A further preferred embodiment will now be described.

The reactor system comprises two reactors in series. The first reactor is charged with a chromia/alumina dehydrogenation catalyst and the second reactor is charged with a ZSM-5 catalyst.

In these experiments propane has been used as the feed gas. The first reactor is operated under conditions which promote maximum selectivity for the production of propene. The product from this reactor, comprising propene, hydrogen, $C_1$-$C_2$ hydrocarbons and predominantly unreacted propane, is passed through the second reactor. This reactor is operated under conditions which promote the conversion of propene, rather than propane, to a product containing aromatic compounds. The liquid aromatic hydrocarbons are then separated from the product, leaving a stream containing hydrogen and $C_1$-$C_5$ hydrocarbons from which the hydrogen and $C_1$-$C_2$ compounds can be further separated to leave a $C_{3+}$ hydrocarbon stream which may be recycled to the first reactor. This stream consists predominantly of unreacted propane but also contains butanes produced during the aromatization of propene.

The results of passing a propane feed through this system under conversion conditions are shown in Table 3. It can be seen that by selecting operating conditions as described above, a product rich in aromatics, with very few $C_1$ to $C_2$ hydrocarbons, is obtained. There is also a significant proportion of butanes present in the product. Examples 2 and 3 in Table 3 show that the production of these butanes can be reduced in favour of aromatics by increasing the temperature of the second reactor, but this also increases production of undesirable $C_1$-$C_2$ hydrocarbons.

A preferred way of reducing butane production in favour of aromatic production in the overall process is by recycling the $C_{3+}$ product stream through the reactor system as mentioned above. Once the liquid aromatic hydrocarbons, hydrogen and $C_1$-$C_2$ hydrocarbons have been removed from the product of the second reactor, this stream consists of 5 to 7 weight percent of butanes, the remainder being unreacted propane. This stream can then be passed through the first reactor to be dehydrogenated to the corresponding olefins which are then in turn aromatized in the second reactor.

Table 4 shows the results of feeding a stream comprising 95 weight percent propane and 5 weight percent butanes through the reactor system. It can be seen that if $C_1$ to $C_2$ hydrocarbon production is to be kept to a minimum, that once again the first reactor must be operated under conditions which provide maximum selectivity towards olefin production and the second reactor under conditions which promote alkene, rather than alkane, to aromatic conversions.

TABLE 3

CONDITIONS AND YIELDS FOR FIRST PASS OF REACTOR SYSTEM

Propane feed
Reactor 1 charged with 100 gm chromia/alumina
Reactor 2 charged with 100 gm H-ZSM-5

| Examples | 1 | 2 | 3 | 4 | 5 |
|---|---|---|---|---|---|
| MHSV of $C_3H_8$ in Reactor 1 (hr$^{-1}$) | 1.18 | 2.36 | 2.36 | 2.95 | 1.18 |
| Temperature of Reactor 1 (°C.) | 550 | 550 | 550 | 550 | 550 |
| Pressure in Reactor 1 (MPa) | 0.1 | 0.1 | 0.1 | 0.1 | 0.05 |
| MHSV of $C_3H_6$ in Reactor 2 (Hr$^{-1}$) | 0.7 | 0.21 | 0.20 | 0.23 | 0.14 |
| Temperature of Reactor 2 (°C.) | 400 | 400 | 450 | 400 | 400 |
| Pressure in Reactor 2 (MPa) | 0.1 | 0.1 | 0.1 | 0.1 | 0.1 |
| $C_3H_8$ Conversion in Reactor 1 (%) | 6.90 | 10.08 | 9.37 | 9.07 | 12.59 |
| $C_3H_8$ Conversion in Reactor 2 (%) | 4.94 | 4.61 | 18.18 | 3.67 | 6.83 |
| $C_3H_6$ Conversion in Reactor 2 (%) | 95.73 | 95.86 | 90.49 | 95.75 | 97.19 |
| *Selectivity to: | | | | | |
| Carbon in Reactor 1 | 0.007 | — | 0.01 | 0.01 | 0.01 |
| Carbon in Reactor 2 | 0.002 | — | 0.002 | 0.002 | 0.003 |
| Methane | 0.04 | 0.03 | 0.08 | 0.03 | 0.03 |
| $C_2$'s | 0.08 | 0.07 | 0.13 | 0.07 | 0.06 |
| Propene | 0.02 | 0.03 | 0.04 | 0.03 | 0.02 |
| i-Butane | 0.21 | 0.23 | 0.15 | 0.26 | 0.24 |
| n-Butane | 0.30 | 0.27 | 0.23 | 0.24 | 0.24 |
| $C_5$'s | 0.04 | 0.08 | 0.03 | 0.07 | 0.04 |
| Aromatics | 0.29 | 0.29 | 0.32 | 0.29 | 0.35 |

*Selectivity defined as in Table 2

TABLE 4

CONDITIONS AND YIELDS FOR SECOND PASS OF REACTOR SYSTEM

Feed comprising 95 wt. % propane and 5 wt. % butanes
Reactor 1 charged with 100 gm chromia/alumina
Reactor 2 charged with 100 gm H-ZSM-5

| Examples | 1 | 2 | 3 | 4 |
|---|---|---|---|---|
| MHSV of $C_3H_8$ and $C_4H_{10}$ in Reactor 1 (hr$^{-1}$) | 1.23 | 1.84 | 1.23 | 1.23 |
| Temperature of Reactor 1 (°C.) | 550 | 550 | 550 | 550 |
| Pressure in Reactor 1 (MPa) | 0.1 | 0.1 | 0.1 | 0.05 |
| MHSV of $C_3H_6$ & $C_4H_8$ in Reactor 2 (hr$^{-1}$) | 0.08 | 0.34 | 0.16 | 0.07 |
| Temperature of Reactor 2 (°C.) | 400 | 400 | 450 | 400 |
| Pressure in Reactor 2 (MPa) | 0.1 | 0.1 | 0.1 | 0.1 |
| *Selectivity to: | | | | |
| Carbon in Reactor 1 | 0.01 | 0.04 | 0.01 | 0.02 |
| Carbon in Reactor 2 | 0.007 | — | 0.004 | — |
| Methane | 0.12 | 0.06 | 0.21 | 0.09 |
| $C_2$'s | 0.20 | 0.11 | 0.20 | 0.17 |
| $C_5$'s | 0.08 | 0.09 | 0.02 | 0.10 |
| Aromatics | 0.58 | 0.69 | 0.52 | 0.62 |

*Selectivity defined as in Table 2

EXPERIMENTAL

Example (1) Catalyst Preparation (a) For Reactor 1

The method of preparation basically follows that given by Archibald and Greensfelder (Industrial and Engineering Chemistry, April, 1945 pages 356 to 361) wherein activated alumina (50 g) was slowly added to a solution of chromic acid (10 g) in distilled water (21 cm$^3$) until the entire solution was absorbed, resulting in moist impregnated alumina. The alumina was then dried in a low temperature oven and calcined at 500° C. for 16 hours before use.

The catalyst was either used as prepared above or modified by the addition of promoters. Typical promoters being cerium or potassium. The potassium promoted catalyst was prepared by slowly adding calcined chromia-alumina catalyst (10 g) to a solution of potassium nitrate (0.3 g) in distilled water (3.5 cm$^3$). The moist catalyst was then dried at a low temperature and calcined at 500° C. for 16 hours before use.

(b) For Reactor 2

Preparation of the ZSM-5 catalyst comprised the addition of 372 g of sodium silicate solution (27.9% SiO$_2$) with 414 g of distilled water, together with 630 g of an aluminum sulphate-sulphuric acid solution (1.87 wt percent Al$_2$(SO$_4$)$_3$ 18H$_2$O, 4.5 wt percent H$_2$SO$_4$), 5 g of ZSM-5 catalyst was added, to act as seed for the crystallization. The mixture was then heated at 175° C. in a glass lined autoclave for 24 hours. The resulting crystalline product was verified by X-ray crystallography as ZSM-5.

The crystalline product was acid washed, filtered and dried. A 10 gm portion of the resultant HZSM-5 was mixed with 130 ml of 0.1M zinc chloride (ZnCl$_2$) solution and heated at 80° C. for 4 hours whilst stirring and then allowed to stand at room temperature overnight. The suspension was filtered, and the catalyst dried at 120° C. and calcined at 540° C. for seven hours. The resulting zinc-exchanged catalyst was designated ZnZSM-5.

We claim:

1. A process for the production of aromatic compounds from propane feedstock which comprises contacting the feedstock in a first reactor with a promoted chromia alumina dehydrogenation catalyst at a temperature between 380° and less than 550° C. to produce a first reaction product containing propylene; contacting said first reaction product in a second reactor with a crystalline aluminosilicate catalyst to produce a second reaction product comprising aromatics and C$_{3+}$ hydrocarbons, and separating an aromatic-rich fraction therefrom; and recycling a gaseous fraction of the second reaction product to the first reactor, said recycled gaseous fraction consisting essentially of one or more C$_{3+}$ hydrocarbons.

2. The process according to claim 1, in which the recycled gaseous fraction consists essentially of propane and one or more butane isomers.

3. The process according to claim 1, in which the feedstock is contacted with the dehydrogenation catalyst in the first reactor at a pressure between 0.01 and 0.50 MPa and mass space velocity between 0.1 and 10 hr$^{-1}$.

4. The process according to claim 3, in which the dehydrogenation catalyst is a promoted catalyst wherein the promotor is selected from the group consisting of potassium, cerium and a mixture thereof.

5. The process according to claim 3, in which the crystalline aluminosilicate catalyst is of the ZSM-5 type.

6. The process according to claim 5, in which the crystalline aluminosilicate catalyst is modified by hydrogen or zinc.

7. The process according to claim 5, in which the first reaction product is contacted with the crystalline aluminosilicate catalyst in the second reactor at a temperature between 220° and 550° C., a pressure between 0.01 and 0.50 MPa and a mass space velocity between 0.1 to 10 hr$^{-1}$.

8. The process according to claim 7, in which the temperature in the second reactor is between 300° and 460° C.

9. A process for the production of aromatic compounds from propane feedstock which comprises contacting the feedstock in a first reactor which a promoted chromia alumina dehydrogenation catalyst at a temperature between 450° and less than 550° C. to produce a first reaction product containing propylene; contacting said first reaction product in a second reactor with a crystalline aluminosilicate catalyst to produce a second reaction product comprising aromatics and C$_{3+}$ hydrocarbons, and separating an aromatic-rich fraction therefrom; and recycling a gaseous fraction of the second reaction product to the first reactor, said recycled gaseous fraction consisting essentially of one or more C$_{3+}$ hydrocarbons.

10. The process according to claim 9, in which the recycled gaseous fraction consists essentially of propane and one or more butane isomers.

11. The process according to claim 9, in which the feedstock is contacted with the dehydrogenation catalyst in the first reactor at a pressure between 0.01 and 0.50 MPa and mass space velocity between 0.1 and 10 hr$^{-1}$.

12. The process according to claim 11, in which the dehydrogenation catalyst is a promoted catalyst wherein the promotor is selected from the group consisting of potassium, cerium and a mixture thereof.

13. The process according to claim 11, in which the crystalline aluminosilicate catalyst is of the ZSM-5 type.

14. The process according to claim 13, in which the crystalline aluminosilicate catalyst is modified by hydrogen or zinc.

15. The process according to claim 13, in which the first reaction product is contacted with the crystalline aluminosilicate catalyst in the second reactor at a temperature between 220° and 550° C., a pressure between 0.01 and 0.50 MPa and a mass space velocity between 0.1 to 10 hr$^{-1}$.

16. The process according to claim 15, in which the temperature in the second reactor is between 300° and 460° C.

* * * * *